United States Patent
Feng et al.

(10) Patent No.: US 10,695,009 B2
(45) Date of Patent: Jun. 30, 2020

(54) SYSTEM AND METHOD FOR DETECTING ORGAN MOTION

(71) Applicant: UIH AMERICA, INC., Houston, TX (US)

(72) Inventors: Tao Feng, Houston, TX (US); Wentao Zhu, Houston, TX (US); Hongdi Li, Houston, TX (US)

(73) Assignee: UIH AMERICA, INC., Houston, TX (US)

(*) Notice: Subject to any disclaimer, the term of this patent is extended or adjusted under 35 U.S.C. 154(b) by 0 days.

(21) Appl. No.: 16/429,185

(22) Filed: Jun. 3, 2019

(65) Prior Publication Data
US 2019/0282186 A1    Sep. 19, 2019

Related U.S. Application Data

(63) Continuation of application No. 15/439,898, filed on Feb. 22, 2017, now Pat. No. 10,307,116.

(51) Int. Cl.
*A61B 6/03*    (2006.01)
*G01T 1/29*    (2006.01)
*A61B 6/00*    (2006.01)

(52) U.S. Cl.
CPC ........... *A61B 6/037* (2013.01); *A61B 6/032* (2013.01); *A61B 6/503* (2013.01); *A61B 6/5205* (2013.01); *A61B 6/5235* (2013.01); *A61B 6/5264* (2013.01); *G01T 1/2985* (2013.01); *A61B 6/465* (2013.01)

(58) Field of Classification Search
CPC ......... A61B 6/037; A61B 6/503; A61B 6/032; A61B 6/5205; A61B 6/465; A61B 6/5235
See application file for complete search history.

(56) References Cited

U.S. PATENT DOCUMENTS

| | | | |
|---|---|---|---|
| 7,574,249 B2 | 8/2009 | Piacsek et al. |
| 8,144,962 B2 | 3/2012 | Busch et al. |
| 8,600,132 B2 | 12/2013 | Razifar et al. |
| 2008/0056550 A1 | 3/2008 | Kadir et al. |
| 2010/0067765 A1 | 3/2010 | Buther et al. |
| 2017/0039738 A1 | 2/2017 | Ziv et al. |
| 2017/0106208 A1 | 4/2017 | Gauthier et al. |

OTHER PUBLICATIONS

Florian Buther et al., List Mode-Driven Cardiac and Respiratory Gating in PET, The Journal of Nuclear Medicine, 50(5): 674-681, 2009.
Yefeng Zheng et al., Four-Chamber Heart Modeling and Automatic Segmentation for 3-D Cardiac CT Volumes Using Marginal Space Learning and Steerable Features, IEEE Transactions on Medical Imaging, 27(11): 1668-1681, 2008.

*Primary Examiner* — David P Porta
*Assistant Examiner* — Fani Boosalis
(74) *Attorney, Agent, or Firm* — Metis IP LLC

(57) ABSTRACT

A system and method of imaging a patient are provided. The system may include an acquisition configured to obtain a PET dataset relating to a target organ of a patient. The system may also include a processing module configured to determine a reference point of the target organ, divide the PET dataset into a plurality of data frames, and determine a motion signal of the target organ based on a plurality of first statistical parameters and a plurality of second statistical parameters. The processing module may further sort the PET dataset into a plurality of bins based on the motion signal.

16 Claims, 12 Drawing Sheets

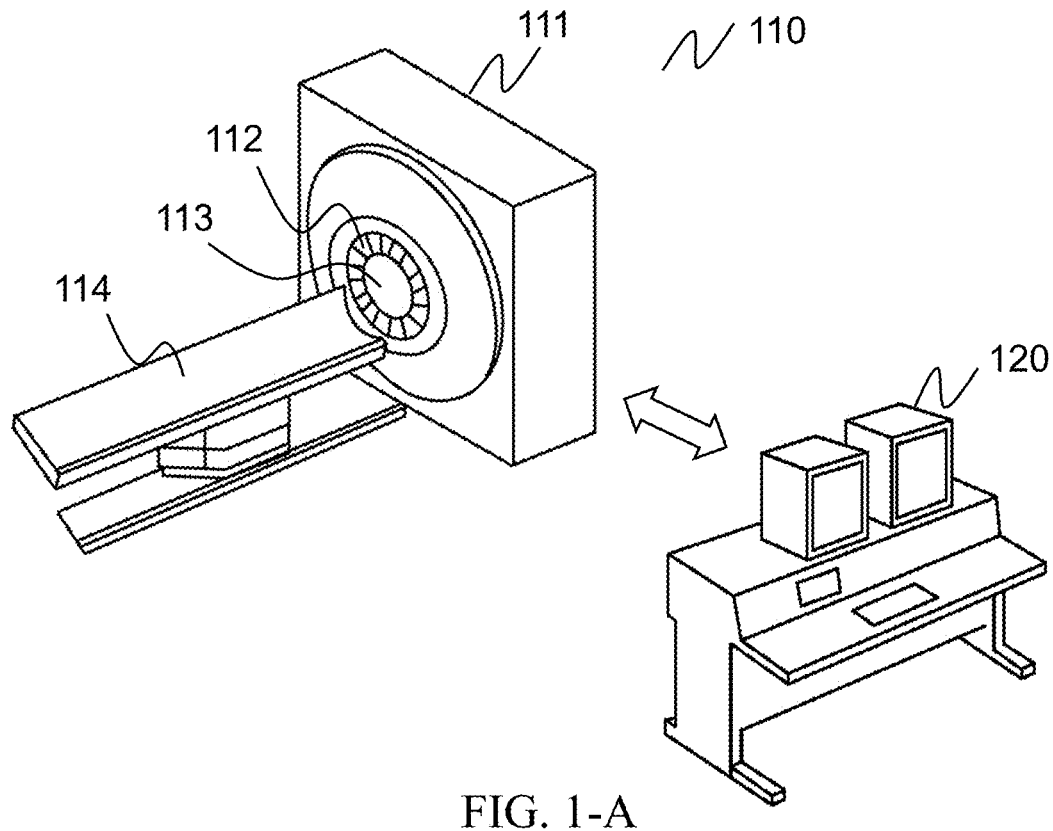
FIG. 1-A
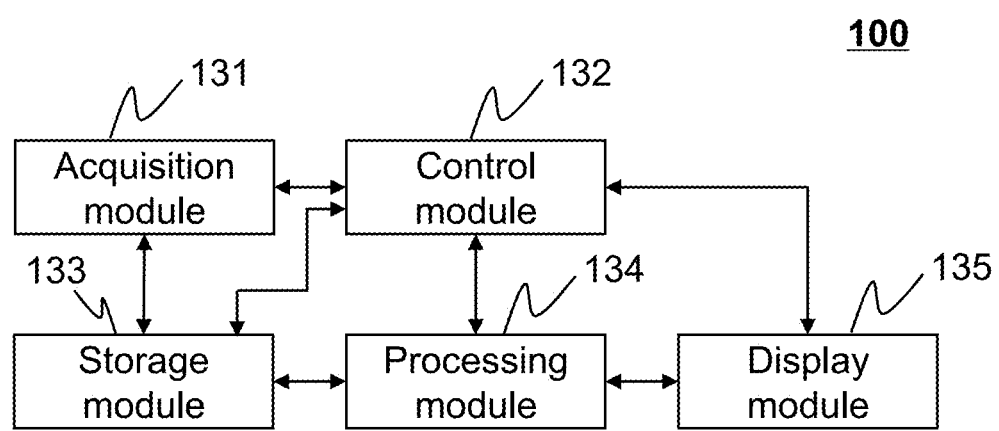
FIG. 1-B

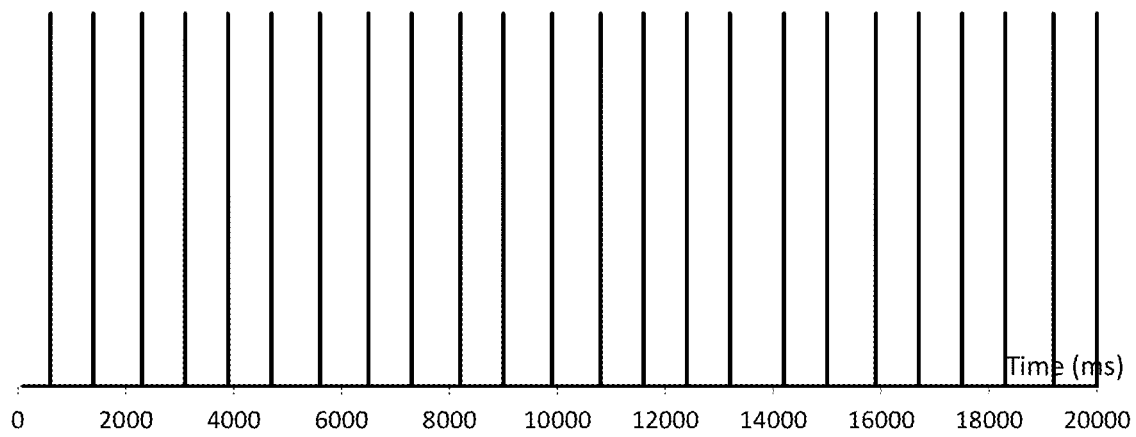
(a)
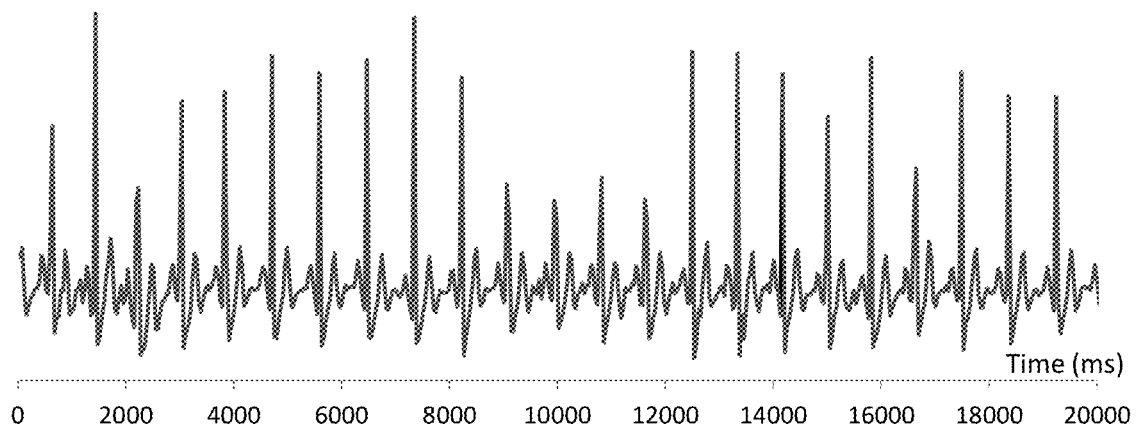
(b)
FIG. 11

SYSTEM AND METHOD FOR DETECTING ORGAN MOTION

CROSS REFERENCE TO RELATED APPLICATIONS

This application is a continuation of U.S. application Ser. No. 15/439,898, filed on Feb. 22, 2017, which is hereby incorporated by reference in its entirety.

TECHNICAL FIELD

The application generally relates to a system and method for detecting organ motion from Emission Computed Tomography (ECT) image, and more specifically relates to a system and method for detecting cardiac gating in Positron Emission Tomography (PET).

BACKGROUND

Emission Computed Tomography (ECT) has been widely used in medicine for diagnosis and other purposes. Types of ECT include Positron Emission Tomography (PET) and Single-Photon Emission Computed Tomography (SPECT). Positron emission tomography (PET) is a specialized radiology procedure that generates three-dimensional images of functional processes in a target organ or tissue of a body. Specifically, in PET studies, a biologically active molecule carrying a radioactive tracer is first introduced to a patient's body. The PET system then detects gamma rays emitted by the tracer and constructs a three-dimensional image of the tracer concentration within the body by analyzing the detected signals. Because the biologically active molecules used in PET studies are natural substrates of metabolism at the target organ or tissue, PET can evaluate the physiology (functionality) and anatomy (structure) of the target organ or tissue, as well as its biochemical properties. Changes in these properties of the target organ or tissue may provide information for the identification of the onset of a disease process before any anatomical changes relating to the disease become detectable by other diagnostic tests, such as computed tomography (CT) or magnetic resonance imaging (MRI).

A subject, such as a patient, may be scanned by an ECT scanner to obtain ECT images. When ECT is used for chest or upper abdomen examinations, respiratory and/or cardiac motions may lead to motion blur in the ECT images. It is desirable to provide systems and methods for reconstructing an ECT image with improved quality and reduced motion blur.

SUMMARY

In an aspect of the present disclosure, a method is provided. The method may include one or more of the following operations. A PET dataset may be obtained, wherein the PET dataset may relate to a target organ of a patient. A reference point of the target organ may be determined. The PET dataset may be divided into a plurality of data frames, wherein at least one of the plurality of data frames relating to a volume of interest which includes a plurality of voxels. A plurality of first statistical parameters about the reference point along a first direction and a plurality of second statistical parameters about the reference point along a second direction may be determined, wherein at least one of the plurality of first statistical parameters may correspond to one of the plurality of data frames, and at least one of the plurality of second statistical parameters may correspond to one of the plurality of data frames. At least one of the plurality of first statistical parameters may be a first variance of coincidence distribution of the plurality of voxels about the reference point and at least one of the plurality of second statistical parameters may be a second variance of coincidence distribution of the plurality of voxels about the reference point. A motion signal of the target organ may be obtained based on the plurality of first statistical parameters and the plurality of second statistical parameters. The PET dataset may be sorted into a plurality of bins based on the motion signal. An image of the target organ may be reconstructed by reconstructing the plurality of bins.

Another aspect of the present disclosure relates to a system. The system may include an acquisition module configured to obtain a PET dataset, wherein the PET dataset may relate to a target organ of a patient. The system may also include a reference point identifying unit configured to determine a reference point of the target organ. The system may also include a pre-processing unit configured to divide the PET dataset into a plurality of data frames, wherein at least one of the plurality of data frames relates to a volume of interest which includes a plurality of voxels. The system may also include a motion identifying unit configured to determine a plurality of first statistical parameters about the reference point along a first direction, a plurality of second statistical parameters about the reference point along a second direction, and obtain a motion signal of the target organ based on the plurality of first statistical parameters and the plurality of second statistical parameters, wherein at least one of the plurality of first statistical parameters may correspond to one of the plurality of data frames, and at least one of the plurality of second statistical parameters may correspond to one of the plurality of data frames. At least one of the plurality of first statistical parameters may be a first variance of coincidence distribution of the plurality of voxels about the reference point and at least one of the plurality of second statistical parameters may be a second variance of coincidence distribution of the plurality of voxels about the reference point. The system may also include a gating unit configured to sort the PET dataset into a plurality of bins based on the motion signal. The system may further include a reconstruction unit configured to generate an image of the target organ by reconstructing the plurality of bins.

As another aspect of the present disclosure, a non-transitory computer readable medium storing instructions may be provided. The instructions, when executed by a computer device, causing the computer device to implement a method including one or more of the following operations. A PET dataset may be obtained, wherein the PET dataset may relate to a target organ of a patient. A reference point of the target organ may be determined. The PET dataset may be divided into a plurality of data frames, wherein at least one of the plurality of data frames relating to a volume of interest which includes a plurality of voxels. For different directions, a plurality of statistical parameters of the plurality of voxels about the reference point may be determined. A motion signal of the target organ may be obtained based on the plurality of statistical parameters. The PET dataset may be sorted into a plurality of bins based on the motion signal. An image of the target organ may be reconstructed by reconstructing the plurality of bins.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a schematic diagram illustrating an exemplary ECT system according to some embodiments of the present disclosure;

FIG. 1-B is a block diagram illustrating an exemplary image processing system according to some embodiments of the present disclosure;

FIG. 11(a) illustrates an exemplary signal of the cardiac motion determined according to some embodiments of the present disclosure, and (b) illustrates a signal measured by an external Electrocardiograph (ECG) device.

DETAILED DESCRIPTION

Figure 2:
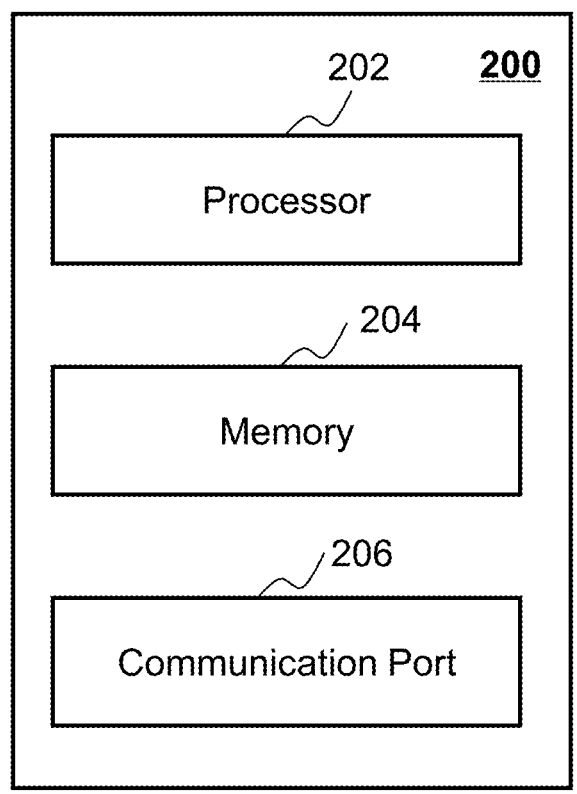
FIG. 2 is a block diagram illustrating exemplary hardware and software components of a computing device according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnostic or research purposes. The imaging system may find its applications in different fields such as medicine or industry. For example, the imaging system may be used in internal inspection of components including, for example, flaw detection, security scanning, failure analysis, metrology, assembly analysis, void analysis, wall thickness analysis, or the like, or any combination thereof.

For illustration purposes, the disclosure describes systems and methods for ECT image reconstruction. The imaging system may reconstruct an ECT image based on a gating method. As used herein, a gating method may refer to that ECT dataset may be divided into a plurality of subsets (also referred to as "data frames") and one of the subsets may be selected to be processed to generate an ECT image. For example, the imaging system may reconstruct an ECT image by applying different gating parameters to the ECT dataset corresponding to different spatial points of a subject. In some embodiments, at least one of the plurality of data frames may relate to a volume of interest which includes a plurality of voxels.

The following description is provided to help better understanding ECT image reconstruction methods or systems. The term "image" used in this disclosure may refer to a 2D image, a 3D image, a 4D image, or any related image data (e.g., the ECT dataset, projection data corresponding to the ECT dataset). The image data may correspond to a distribution of ECT tracers within the subject (e.g., a patient) or a coincidence distribution of the plurality of voxels within the subject represented in sonogram. As used herein, the ECT tracer may refer to a substance that may undergo certain changes under the influence of an activity or functionality within the subject, whose activity and/or functionality are to be visualized and/or studied. This is not intended to limit the scope the present disclosure. For persons having ordinary skills in the art, a certain amount of variations, changes, and/or modifications may be deducted under guidance of the present disclosure. Those variations, changes, and/or modifications do not depart from the scope of the present disclosure.

FIG. 1-A is a schematic diagram illustrating an exemplary ECT system according to some embodiments of the present disclosure. The ECT system may include a positron emission tomography (PET) system, or a single photon emission computed tomography (SPECT) system. Exemplary multi-modality system may include a computed tomography-positron emission tomography (CT-PET) system, a magnetic resonance-positron emission tomography (MR-PET) system, etc. In some embodiments, the multi-modality imaging system may include modules and/or components for performing ECT imaging and/or related analysis.

The ECT system may include an ECT scanner 110 and a host computer 120. ECT scanner 110 may include a gantry 111, a detector 112, a detecting region 113, and a subject table 114.

Detector 112 may detect radiation events (e.g., gamma photons) emitted from detecting region 113. In some embodiments, detector 112 may include a plurality of detector units. The detector units may be implemented in any suitable manner, for example, a ring, a rectangle, or an array. In some embodiments, the detector unit may include one or more crystal elements and/or one or more photomultiplier tubes (PMT) (not shown). In some embodiments, a PMT as employed in the present disclosure may be a single-channel PMT or a multi-channel PMT. Subject table 114 may position a subject in detecting region 113.

In some embodiments, the detected radiation events may be stored or archived in a storage (e.g., a storage device in host computer 120), displayed on a display (e.g., a display of or attached to host computer 120), or transferred to an external storage device (e.g., an external storage device attached to host computer 120 via a cable, or a wired or wireless network). In some embodiments, a user may control ECT scanner 110 via host computer 120.

Further, while not shown, the ECT system may be connected to a network (e.g., a telecommunications network, a local area network (LAN), a wireless network, a wide area network (WAN) such as the Internet, a peer-to-peer network, a cable network, etc.) for communication purposes.

It should be noted that the above description of the ECT system is merely provided for the purposes of illustration, and not intended to limit the scope of the present disclosure. For persons having ordinary skills in the art, multiple variations and modifications may be made under the teachings of the present disclosure. For example, the assembly and/or function of the ECT system may be varied or changed according to specific implementation scenarios. Merely by way of example, some other components may be added into the ECT system, such as a patient positioning module, a gradient amplifier module, and other devices or modules. As another example, storage module 133 may be optional and the modules in the ECT system may include an integrated storage unit respectively.

FIG. 1-B is a block diagram illustrating an exemplary image processing system 100 according to some embodiments of the present disclosure. Image processing system 100 may be implemented via host computer 120. As illustrated in FIG. 1-B, image processing system 100 may include an acquisition module 131, a control module 132, a storage module 133, a processing module 134, and a display module 135.

Acquisition module 131 may acquire or receive ECT dataset. Merely by way of example with reference to a PET system, acquisition module 131 may acquire or receive PET data. In some embodiments, during a PET scan or analysis, PET tracer (also referred to as "PET tracer molecules") are first introduced into the subject before an imaging process begins. During the PET scan, the PET tracer molecules may emit positrons, namely the antiparticles of electrons. A positron has the same mass and the opposite electrical charge as an electron, and it undergoes an annihilation (also referred to as an "annihilation event" or a "coincidence event") with an electron (that may naturally exist in abundance within the subject) as the two particles collide. An electron-positron annihilation may result in two 511 keV gamma photons, which, upon their own generation, begin to travel in opposite directions with respect to one another. The line connecting the two gamma photons may be referred to as a "line of response (LOR)." Acquisition module 131 may obtain the trajectory and/or information of the gamma photons (also referred to as the "PET data"). For example, the PET data may include a list of annihilation events, transverse and longitudinal positions of the LORs, or the like, or a combination thereof. In some embodiments, the PET data may be used to determine the distribution of the PET tracer molecules in image domain and/or the coincidence distribution of voxels in sonogram coordinate).

In some embodiments, the PET tracer may include carbon (11C), nitrogen (13N), oxygen (15O), fluorine (18F), or the like, or a combination thereof. In some embodiments, for a SPECT system, a SPECT tracer may be introduced into the subject. The SPECT tracer may include technetium-99m, iodine-123, indium-111, iodine-131, or the like, or a combination thereof. Accordingly, in some embodiments, the PET tracer or SPECT tracer of the present disclosure may be organic compounds containing one or more of such isotopes. These tracers are either similar to naturally occurring substances or otherwise capable of interacting with the functionality or activity of interest within the subject. Hence, distributional information of the tracer may be reliably used as an indicator of the subject functionality. In some embodiments, the PET tracer and the SPECT tracer may be collectively referred to as "ECT tracer."

Control module 132 may generate a control parameter for controlling acquisition module 131, storage module 133, processing module 134, and/or display module 135. For example, control module 132 may control acquisition module 131 as to whether to acquire a signal, or the time when a signal acquisition may occur. As another example, control module 132 may control processing module 134 to select different algorithms to process the ECT dataset acquired by acquisition module 131. In some embodiments, control module 132 may receive a real-time or a predetermined command provided by a user (e.g., a doctor) and adjust acquisition module 131, and/or processing module 134 to take images of a subject according to the received command. In some embodiments, control module 132 may communicate with other modules in image processing system 100 for exchanging information or data.

Storage module 133 may store the acquired ECT dataset, the control parameters, the processed ECT dataset, or the like, or a combination thereof. In some embodiments, storage module 133 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, storage module 133 may store one or more programs and/or instructions that may be executed by one or more processors of image processing system 100 (e.g., processing module 134) to perform exemplary methods described in this disclosure. For example, storage module 133 may store program(s) and/or instruction(s) executed by the processor(s) of image processing system 100 to acquire ECT dataset, reconstruct an image based on the ECT dataset, or display any intermediate result or a resultant image.

Processing module 134 may process information received from modules in image processing system 100. In some embodiments, processing module 134 may process the ECT dataset acquired by acquisition module 131, or retrieved from storage module 133. In some embodiments, processing module 134 may reconstruct ECT images based on the ECT dataset, generate reports including one or more ECT images and/or other related information, or the like. For example, processing module 134 may process the ECT dataset based on a gating approach and reconstruct an ECT image based on the gated ECT dataset. As another example, processing module 134 may determine a plurality of gating parameters for the ECT dataset corresponding to a plurality of spatial points of the subject (e.g., chest, back, or the like).

Display module 135 may display any information relating to image processing system 100. The information may include programs, software, algorithms, data, text, number, images, voice, or the like, or any combination thereof. In some embodiments, display module 135 may include a liquid crystal display (LCD), a light emitting diode (LED) based display, a flat panel display, a cathode ray tube (CRT), a touch screen, or the like, or a combination thereof. The touch screen may include, for example, a resistance touch screen, a capacity touch screen, a plasma touch screen, a vector pressure sensing touch screen, an infrared touch screen, or the like, or a combination thereof.

In some embodiments, one or more modules illustrated in FIG. 1-B may be implemented in at least part of the exemplary ECT system illustrated in FIG. 1-A. For example, acquisition module 131, control module 132, storage module 133, processing module 134, and/or display module 135 may be integrated into a console. Via the console, a user may set parameters for scanning, control the imaging procedure, control a parameter of the reconstruction of an image, view the reconstructed images, etc. In some embodiments, the console may be implemented via host computer 120.

FIG. 2 is a block diagram illustrating exemplary hardware and software components of computing device 200 on which image processing system 100 may be implemented according to some embodiments of the present disclosure. In some embodiments, computing device 200 may include a processor 202, a memory 204, and a communication port 206.

Processor 202 may execute computer instructions (program code) and perform functions of processing module 134 in accordance with techniques described herein. Computer instructions may include routines, programs, objects, components, data structures, procedures, modules, and functions, which perform particular functions described herein. For example, processor 202 may process the data or information received from acquisition module 131, control module 132, storage module 133, or any other component of imaging system 100. In some embodiments, processor 202 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, processor 202 may include a microcontroller to process the ECT dataset from ECT scanner 110 for image reconstruction.

Memory 204 may store the data or information received from acquisition module 131, control module 132, storage module 133, processing module 134, or any other component of imaging system 100. In some embodiments, memory 204 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, memory 204 may store one or more programs and/or instructions to perform exemplary methods described in the present disclosure. For example, memory 204 may store a program for processing module 134 for reconstructing an ECT image based on the ECT dataset.

Communication port 206 may transmit to and receive information or data from acquisition module 131, control module 132, storage module 133, processing module 134 via network. In some embodiments, communication port 206 may include a wired port (e.g., a Universal Serial Bus (USB) port, a High Definition Multimedia Interface (HDMI) port, or the like) or a wireless port (a Bluetooth port, an infrared interface, a WiFi port, or the like).

Figure 3:
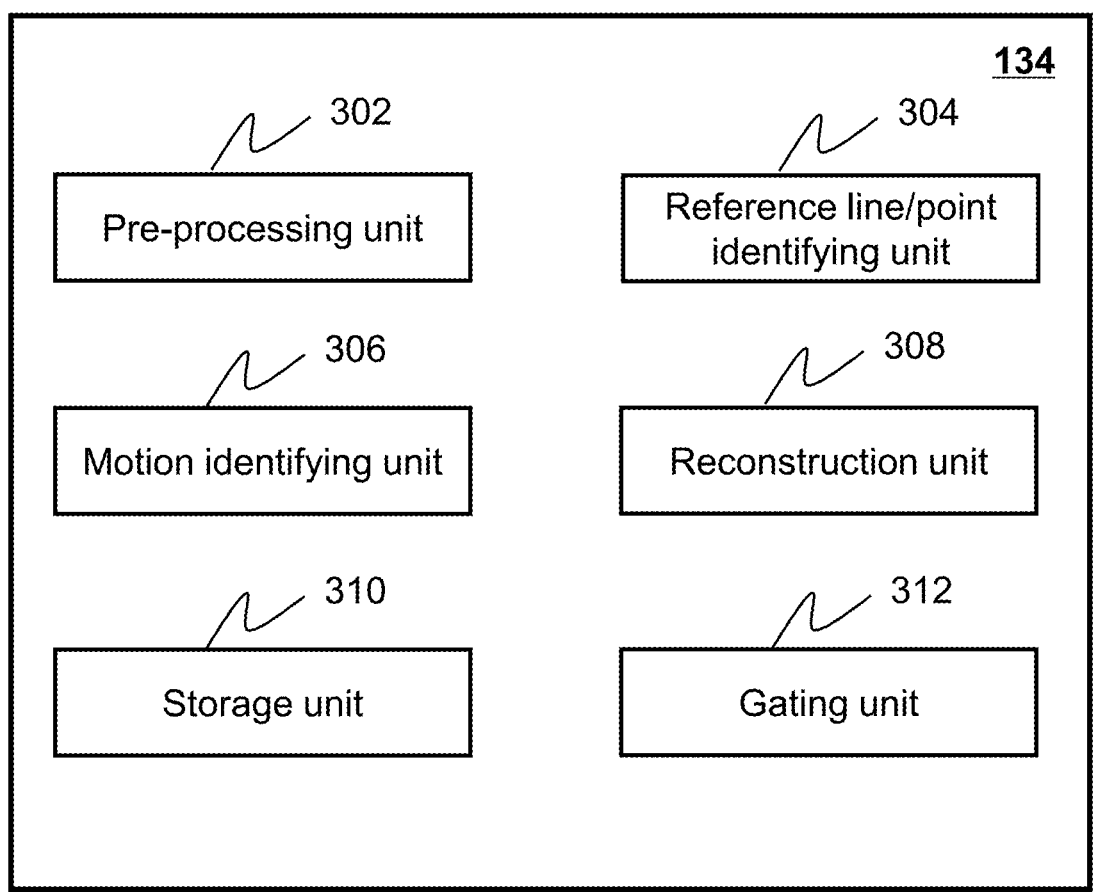
FIG. 3 is a block diagram of an exemplary processing module according to some embodiments of the present disclosure.

FIG. 3 is a block diagram of exemplary processing module according to some embodiments of the present disclosure. Processing module 134 may include a pre-processing unit 302, a reference line/point setting unit 304, a motion identifying unit 306, a reconstruction unit 308, a storage unit 310, and a gating unit 312. In some embodiments, the units may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or a combination thereof).

Pre-processing unit 302 may pre-process information received from acquisition module 131, control module 132, storage module 133, and/or display module 135. In some embodiments, the information may include the ECT (coincidence) dataset, a control parameter (e.g., acquisition frequency, acquisition speed, or the like), etc. For example, pre-processing unit 302 may pre-process the ECT dataset received from acquisition module to, for example, reduce noises. As another example, pre-processing unit 302 may divide the ECT dataset into a plurality of subsets (also referred to as "data frames") corresponding to a plurality of time frames. Furthermore, pre-processing unit 302 may construct sinograms based on at least portions of the subsets for subsequent processing of the ECT dataset. In some embodiments, the information may include information regarding a subject (e.g., a patient) being scanned. The information may be real-time or historical. For example, pre-processing unit 302 may pre-process an image (e.g., a CT image) of the subject being scanned. Specifically, the image of the subject may be a real-time image reconstructed before the acquisition of the ECT dataset, or based on the acquisition of the ECT dataset. In some embodiments, pre-processing the image of the subject may include determining the shape or position of the subject.

Reference line/point identifying unit 304 may identify a reference line in a sinogram constructed based on the ECT dataset, or a reference point (e.g., the central point) relating to the subject. The reference line in the sinogram may correlate with the reference point relating to the subject. In some embodiments, the reference line may be identified directly in the sinogram. In some embodiments, the reference line may be identified according to the reference point relating to the subject. The identification of the reference line/point will be discussed in details below.

Motion identifying unit 306 may identify the motion of a subject (e.g., an organ of a patient) being scanned based on the ECT dataset. In some embodiments, motion identifying unit 306 may identify the motion by determining motion parameters of the subject at different time points. For example, motion parameters relating to two or more data frames divided by pre-processing unit 302 may be determined. In some embodiments, the two or more data frames selected may be continuous in time such that the motion parameters may reflect the motion of the subject in a continuous manner. In some embodiments, the two or more subsets selected may be discontinuous in time such that the motion parameters may reflect motion of the subject in other specific manners. Exemplary motion parameters may include a motion parameter relating to the center of mass or the center of the subject. In some embodiments, the motion parameters may include statistical parameters in the form of, for example, a second-order moment (e.g., the rotational inertia), a fourth-order moment (e.g., the kurtosis), or any other order moments. The motion parameters in the form of second-order moment are also referred to as expansion-parameters in the present disclosure. To determine the motion parameters, motion identifying unit 306 may set a volume of interest (VOI), within which the motion parameters may be determined. Furthermore, different kinds of modifications may be applied in the determination of the motion parameters to characterize the motion of the subject along a specific direction. For illustration purpose, probabilistic distribution of time-of-fly (TOF) may be utilized to optimize the acquired data and/or the direction of motion according to which the motion parameter of the subject is determined. The probability distribution may be estimated based on one or more probability models including a Bernoulli distribution, a Poisson distribution, a uniform distribution, an exponential distribution, a normal distribution, or the like, or a combination thereof.

Reconstruction unit 308 may reconstruct an image. In some embodiments, reconstruction unit 308 may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or a combination thereof. In some embodiments, reconstruction unit 308 may employ different kinds of imaging reconstruction techniques for the image reconstruction procedure. Exemplary image reconstruction techniques may include Fourier reconstruction, constrained image reconstruction, regularized image reconstruction in parallel MRI, or the like, or a variation thereof, or a combination thereof. In some embodiments, reconstruction unit 308 may use different reconstruction algorithms including an analytic reconstruction algorithm or an iterative reconstruction algorithm for the image reconstruction procedure. Exemplary analytic reconstruction algorithms may include a filter back projection (FBP) algorithm, a back projection filter (BFP) algorithm, a ρ-filtered layer gram, or the like, or a combination thereof. Exemplary iterative reconstruction algorithms may include a Maximum Likelihood Expectation Maximization (ML-EM), an Ordered Subset Expectation Maximization (OSEM), a Row-Action Maximum Likelihood Algorithm (RAMLA), a Dynamic Row-Action Maximum Likelihood Algorithm (DRAMA), or the like, or a combination thereof.

In some embodiments, reconstruction unit 308 may reconstruct an image based on the acquired ECT dataset or a subset thereof. For example, reconstruction unit 308 may reconstruct a PET image based on at least one subset of ECT dataset acquired via acquisition module 131. As another example, reconstruction unit 308 may reconstruct a PET image based on ECT dataset processed by taking the motion of subject into account (e.g., gated ECT dataset). In some embodiments, when a CT-PET multi-modality system is used, reconstruction unit 308 may reconstruct a CT image based on the CT scanning data to display the shape and/or position of the subject. Furthermore, the CT scanning data or the CT image may be used for attenuation correction of a PET or SPET scan.

Storage unit 310 may store data or information generated by pre-processing unit 302, reference line/point identifying unit 304, motion identifying unit 306, reconstruction unit 308, or gating unit 312. Exemplary data or information may include the ECT dataset, models to pre-process different kinds of information or identify the reference line/point, control parameters for operation of different units, computing results, determination algorithms for identifying the motion of subject, or the like, or a combination thereof. It shall be noted that storage module 310 may be unnecessary, and any storage disclosed anywhere in the present disclosure may be used to store the data or information mentioned above. For example, storage module 133 may share a common storage with the system 100.

Gating unit 312 may gate the ECT dataset. In some embodiments, the ECT dataset may be gated based on a motion signal or a denoised motion signal relating to the subject that produces the ECT dataset. As used herein, "gate" may refer to that the ECT dataset may be classified into a plurality of bins (also referred to as "gated data") corresponding to a plurality of time intervals. Merely by way of example, the ECT dataset may be classified into two bins, one of the bins may correspond to, for example, the peak of physiological motion (e.g., cardiac motion), and the other bin may correspond to, for example, the valley of physiological motion. In some embodiments, gated data over successive time intervals may be processed to produce a simulation of physiological movement.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, storage unit 310 may be integrated in any unit of processing module 134. As another example, each of the unit in processing module 134 may access to a storage medium of image processing system 100, or a storage medium external to image processing system 100. As a further example, the units may be partially integrated in one or more independent units or share one or more sub-units.

Figure 4:
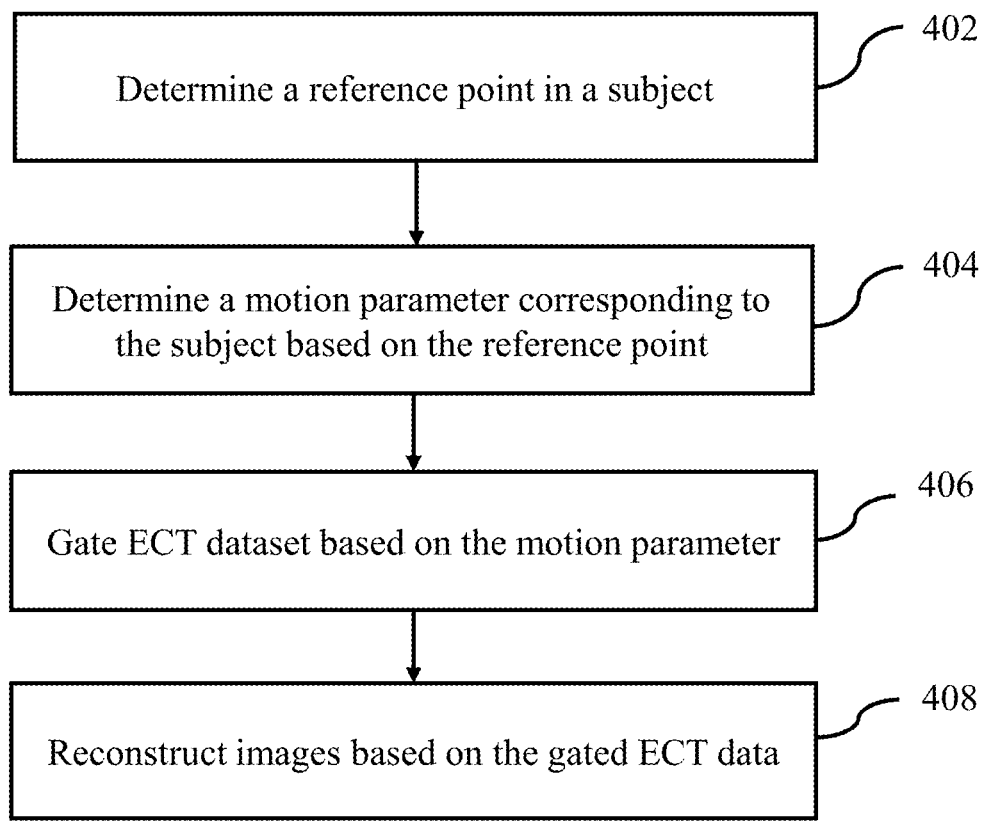
FIG. 4 is a flowchart illustrating an exemplary process of reconstructing an image according to some embodiments of the present disclosure.

FIG. 4 is a flowchart illustrating an exemplary process of reconstructing an image according to some embodiments of the present disclosure.

In 402, a reference point in a subject may be determined. The reference point may be identified by reference line/point identifying unit 304. In some embodiments, the reference point may be a specific point in the subject. For example, the reference point may be a central point in a target organ (e.g., a heart) or a portion thereof (e.g., a chamber of a heart). The determination of the reference point may be found elsewhere in the disclosure, e.g., FIG. 5 and the description thereof.

In some embodiments, the reference point may correspond to a specific line in the sonogram. Merely by way of example with reference to a PET system, a sinogram according to PET dataset may be constructed. A coincidence event pair of an annihilation event that identifies a corresponding line of response (LOR) may be identified by an angle and a distance from a center of the field view in the plane of a detector ring (e.g., the x-y plane illustrated in FIG. 9). As used herein, the sinogram may represent the array of the responses identified by the angle and the distance. The sinogram may be constructed based on one or subsets of ECT dataset corresponding to a subject being scanned as described above. In some embodiments, the reference line may be obtained by correlating a sinusoidal/cosinusoidal curve in the sinogram with the reference point. The reference line may be identified by various methods in accordance with some embodiments of the present disclosure. For example, when the reference point is the central point in the subject, the reference line may be identified directly from the sinogram by identifying a sinusoidal/cosinusoidal curve with a relatively small magnitude (e.g., a magnitude smaller than a threshold).

In 404, a motion parameter relating to the subject may be determined based on the reference point. The motion parameter may be determined by motion identifying unit 306. The motion parameter may correspond to a characterization of ECT tracer in the subject. Merely by way of example, the motion parameter may be determined by a statistical parameter in a VOI determined by the shape and/or position of the subject (e.g., the heart). In some embodiments, the VOI may represent a standardized region with a plurality of voxels that includes the subject. In some embodiments, the motion parameters may include statistical parameters of coincidence distribution of the plurality of voxels about the reference point in sonogram coordinate. In some embodiments, the motion parameters may include statistical parameters of tracer distribution of the plurality of voxels about the reference point in image domain. In some embodiments, the statistical parameters of coincidence distribution or the statistical parameters of tracer distribution may be determined by a second-order moment, a fourth-order moment, or any other order moments of the voxels in the VOI about the reference point.

In 406, ECT dataset may be gated based on the motion parameter. The gating may be performed by gating unit 312. A motion may occur within a specific time interval, in which the acquired ECT dataset may be screened out and designated as different motion-related data. In some embodiments, a gating threshold may be set that the amplitude of the motion parameter exceeding the gating threshold may be screened out, and the corresponding data or signals may be designated as a first motion-state related data. Similarly, the amplitude of the motion parameter below the threshold may be screened out, and the corresponding data or signals may be designated as a second motion-state related data. For example, the ECT dataset relating to a cardiac motion may be gated into different time intervals including systolic time interval and diastolic time interval. In some embodiments, the gating threshold may be set based on a default setting of image processing system 100 or an input from an operator (e.g., a doctor). In some embodiments, the gating threshold may be adjusted. For instance, as the cardiac motion of a subject in a resting state is different from the cardiac motion of the subject in an exercising state, the gating threshold applied when the subject is in a resting state may be adjusted by, for example, the image processing system 100 or an operator, to a value greater than the gating threshold applied when the subject is in an exercising state. In some embodiments, the adjustment of the gating threshold may be achieved by a trigger instruction (e.g., a trigger pulse on a chip) when a different cardiac motion is detected or designated. The trigger instruction may be preset by the image processing system 100.

In 408, images may be reconstructed based on the gated ECT dataset. The reconstruction may be performed by reconstruction unit 308. After gating the ECT dataset, the ECT data in different bins corresponding to different time intervals may be reconstructed to form different images corresponding to the different motion states. For example, a systolic image may be reconstructed by data in a systolic time interval, and a diastolic image may be reconstructed by data in a diastolic time interval. Furthermore, the reconstructed images or corresponding gated data over successive time intervals may be processed to produce a simulation of physiological movement.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, gating ECT dataset in 406 may be replaced by gating sinograms corresponding to the ECT dataset, and then the reconstruction of images in 408 may be based on the gated sinograms. For another example, a storing step or a caching step may be added between any two steps, in which signals or intermediate data may be stored or cached.

Figure 5:
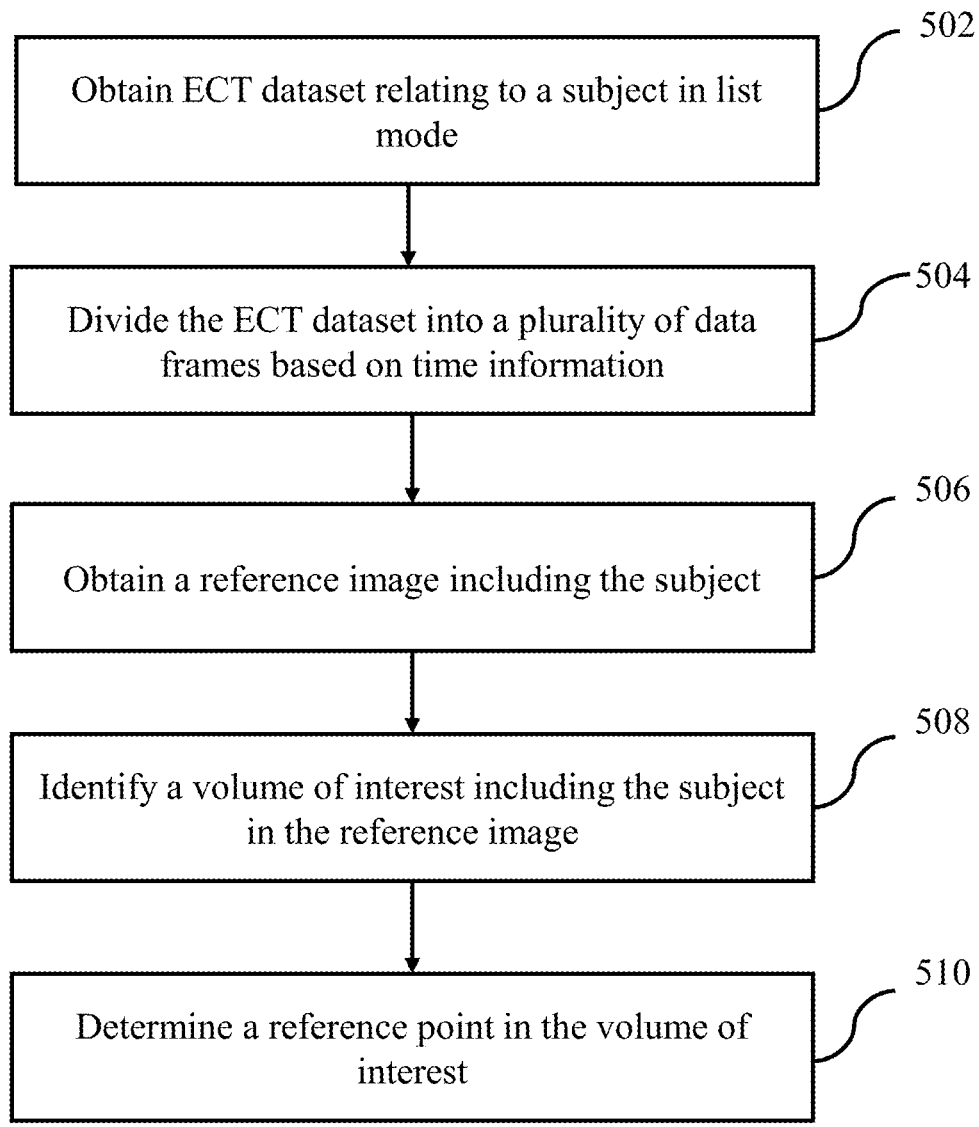
FIG. 5 is a flowchart illustrating the determination of a reference point according to some embodiments of the present disclosure.

FIG. 5 is a flowchart illustrating the designation of a reference point in a subject according to some embodiments of the present disclosure. In some embodiments, the reference point determined in 402 may be obtained through process 500. In some embodiments, the reference point identified herein may be further processed as described above in connection with step 402.

In 502, ECT dataset relating to a subject may be obtained in the list mode. For illustration purpose, the ECT dataset may be acquired by acquisition module 131 from, for example, a PET/CT system. As used herein, the "list mode" may represent a capture by the PET detector of coincidence event pairs in the form of an ordered event list, such as a chronologically ordered event list.

In 504, the ECT dataset may be divided into a plurality of data frames based on time information. The time information may include time stamps that indicate when the coincidence events (also represented by LORs) occur. The ECT dataset may be stored into a time frame [t, t+Δt] if the events occur within that time range. In some embodiments, t may equal to n (an integer) times Δt such that one data frame may have a time interval of Δt. Alternatively, the time range of one data frame may be different from another. The values of Δt for different subjects (e.g., for different patients) may be the same or different. The Δt may be pre-set by default in the PET/CT system, or may be adjusted by a user (e.g., a doctor) or the PET/CT system according to various factors. Exemplary factors may include the physiological state of the subject relating to, for example, the age, the gender, the medical history, the race, etc., of the patient. Specifically, the adjustment of Δt for a specific patient may be based on the historical data of the patient stored in a database. An exemplary value of Δt may be 100 ms, which may be adjusted according to different situations as described above.

In 506, a reference image including the subject may be obtained. In some embodiments, the reference image may be obtained by reference line/point identifying unit 304. In the PET/CT system, the reference image may be a CT image, a PET image, or any other images generated from a medical scanning. A CT image may be obtained by performing a CT scanning on the subject before or after the PET scanning in the PET/CT system. A PET image may be obtained by performing an image reconstruction process on the ECT dataset obtained in 502, the ECT dataset in a data frame in 504 or the sinogram(s) generated in 506. Alternatively, the CT image or PET image may be a historical image of the subject being scanned, which is stored in a database corresponding to the patient.

In 508, a volume of interest including the subject may be identified in the reference image. In some embodiments, the volume of interest may be identified by reference line/point identifying unit 304. For illustration purpose, the processing on a CT image is described herein, while it shall be noted that the description is not intent to limit the scope of the disclosure. When a CT image relating to a subject (i.e., a heart) is obtained, the image may include a volume of interest (e.g., the heart region) and other regions. The volume of interest may be identified for subsequent processing via a certain segmentation process.

The segmentation process may be performed by determining one or more characteristics or features of one or more pixels and/or voxels in the image. In some embodiments, exemplary characteristics or features may include gray level, mean gray level, gray value, texture, color, contrast, brightness, or the like, or any combination thereof. In some embodiments, a spatial property of a pixel and/or voxel may also be considered in a segmentation process. Merely by way of example, the segmentation technique may include a region-based segmentation, an edge-based segmentation, a wavelet transform segmentation, a mathematical morphology segmentation, an artificial neural network-based segmentation, a genetic algorithm-based segmentation, or the like, or a combination thereof. The region-based segmentation may base on a threshold segmentation algorithm, cluster analysis, region growing, or the like, or a combination thereof. The threshold segmentation algorithm may include global threshold algorithm (e.g. P-quantile algorithm, an iterative algorithm, concave histogram analysis, the Otsu's algorithm, a fuzzy set algorithm, a two-dimensional entropy thresholding algorithm, a histograms threshold technique, a relaxation algorithm, etc.), a local threshold algorithm, and a multi-threshold algorithm (e.g. a wavelet-based multi-threshold algorithm, a boundary-point-based recursive multi-threshold algorithm, etc.), or the like, or a combination thereof. The cluster analysis may include a K-means algorithm, a fuzzy C-means clustering (FCM) algorithm, etc. The mathematical morphology segmentation may be based on a Hysen points enhanced model, a Hysen line enhanced model, a multiscale Gaussian template matching model, a multi-scale morphological filtering model, etc. The edge-based segmentation may be based on a differential operator (e.g. the Robert operator, the Sobel operator, the Prewitt operator, the Log operator, the Canny operator, etc.), a surface-based fitting, a boundary and surface-based fitting, a serial boundary searching, or the like, or a combination thereof.

In some embodiments, to obtain the heart region, the left lung region may be initially segmented out. The segmentation of the left lung may be performed on a threshold algorithm described above. Then, based on the body structure information of the specific patient or human beings (e.g., the relative position of heart and left lung), the heart region may be determined. In some embodiments, the heart region may have a roughly similar shape of a real heart.

In 510, a reference point in the volume of interest may be determined. The reference point may be determined manually by a user, or automatically by reference line/point identifying unit 304 in the PET/CT system. In some embodiments, the determination of the reference point may be based on the geometrical profile of the volume of interest (e.g., the shape of the heart). In some embodiments, the reference point may be determined by an algorithm depending on the characteristics of the subject. In some embodiments, the reference point may be the central point of the subject or the volume of interest.

In some embodiments, the reference point may be determined based on a machining learning process. For illustrative purpose, when the central point of a heart is to be determined, a classifier may be trained via a learning process. Merely by way of examples, a set of positive training samples and negative training samples may be provided in training the classifier. As used herein, a positive training sample may represent that a correct central point of heart is identified in a training sample, and a negative training sample may represent that an incorrect central point of heart is identified in a training sample. Then, a plurality of points (e.g., voxels in the volume of interest) may be tested one by one using the trained classifier, and different scores corresponding to each of the plurality of points may be assigned by the trained classifier. As a result, the voxel corresponding to the highest score may be identified as the central point of the heart.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more steps may be after some of the steps. For example, a sinogram corresponding to at least one of the plurality of data frames may be generated after 504. As described elsewhere in the disclosure, the sinograms may be generated based on the angle and distance of the LORs with respect to the center of the field of view in the plane of a detector ring. A sinogram may be generated based on all the ECT dataset or a portion thereof stored in one or more data frames divided as described above with respect to 504. Furthermore, a line in the sinogram may be correlated with the central point of the volume of interest (e.g., the heart region). In some embodiments, the line in the sinogram representing the central point of the volume of interest may be converted to the central point by reference line/point identifying unit 304. The conversion may be performed based on a projection equation. As described elsewhere in the disclosure, the line may be identified through, for example, a correlation between the sinogram and the volume of interest in the image. For example, the central point identified may be represented as $(x_c, y_c, z_c)$ in the x-y-z coordinate, and the corresponding line in the sinogram may be represented as $(s_c(\varphi), z_c)$, wherein $s_c$ and $\varphi$ denote the projection of points in the x-y-z coordinate into sinogram coordinate. The description of the correlation between x-y-z coordinate and sinogram coordinate will be further described below. Also, the correlated line may be designated as reference line by reference line/point identifying unit 304. Sequential processes (e.g., as illustrated in FIG. 4) based on the reference line may be performed to determine the motion information of the subject.

Figure 6:
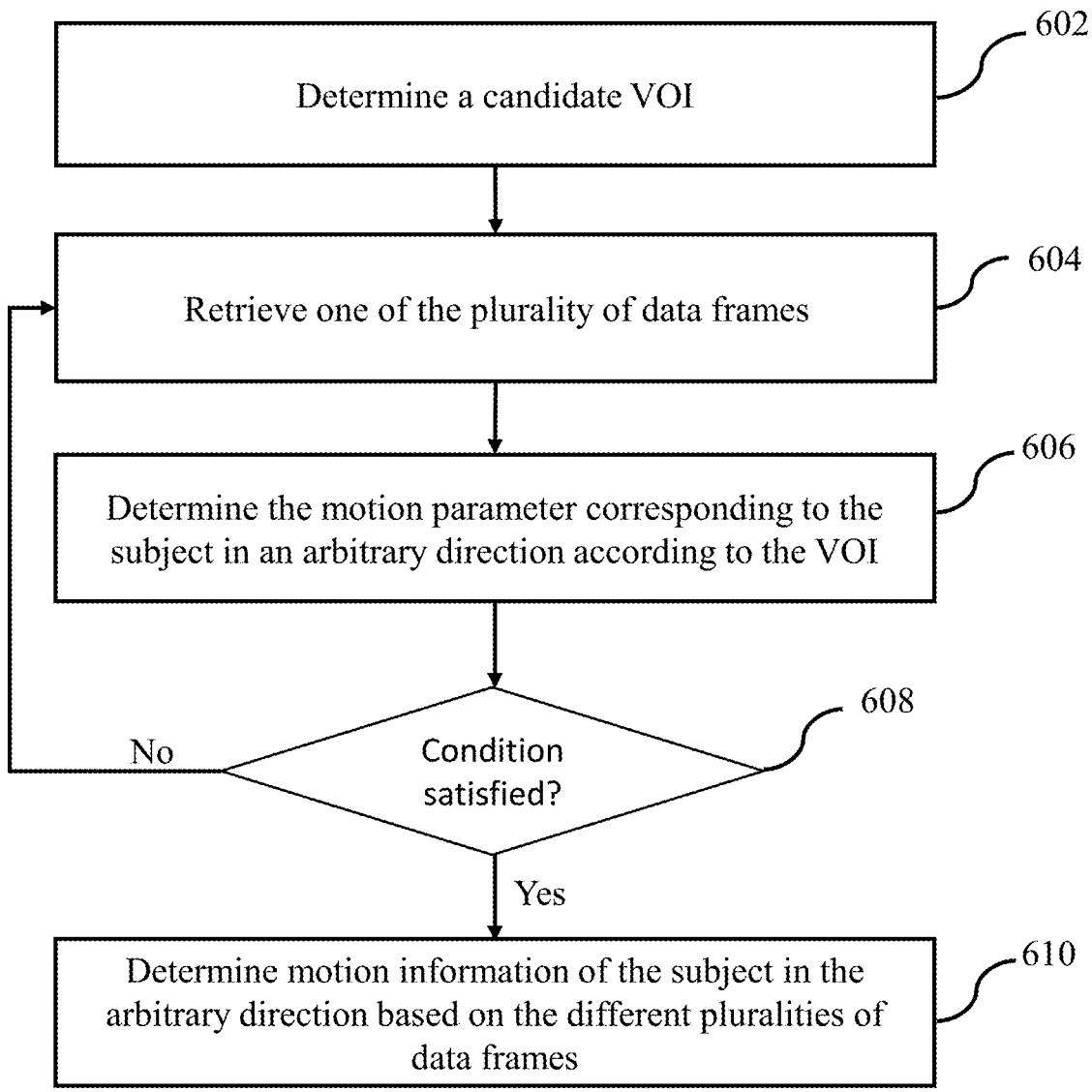
FIG. 6 is a flowchart illustrating an exemplary process of obtaining motion information of a subject according to some embodiments of the present disclosure.

FIG. 6 is a flowchart illustrating an exemplary process of obtaining motion information of a subject according to some embodiments of the present disclosure. In some embodiments, process 600 may be performed by motion identifying unit 306. Process 600 may be performed by processing logic including hardware (e.g., circuitry, dedicated logic, programmable logic, microcode, etc.), software (e.g., instructions run on a processing device to perform hardware simulation), or the like, or a combination thereof. In some implementations, process 600 may be performed by one or more processing devices (e.g., motion identifying unit 306) described elsewhere in the present disclosure.

In 602, a VOI may be determined. In some embodiments, the determination of a VOI may be performed by motion identifying unit 306. In some embodiments, the VOI may be determined after a reference line or a reference point (e.g., a central point) is identified (e.g., as illustrated in FIG. 5). For example, the VOI may be a volume designated around the reference point to enclose the whole subject or a portion of the subject. The VOI may be set manually by a user, or may be set by the system according to a specific algorithm. For illustration purpose, when a central point is determined in the heart region, a VOI in the form of a cylinder may be determined, with the central point located in the center of the cylinder. The diameter and the height of the cylinder may be determined such that the VOI may include the heart region. Merely by way of example, the diameter may be set as 20 cm. In some embodiments, the VOI may be determined by default according to, for example, the characteristic of the subject. For example, a 3-D shape identical to or similar with the subject may be determined as the VOI. As another example, the VOI may be exactly same as the subject that may be segmented by a segmentation process as described elsewhere in this disclosure.

It shall be noted to a person having ordinary skills in the art that the VOI may be in any suitable shape, including regular shapes and irregular shapes. Exemplary regular shapes may include a spherical shape, a cuboid, an ellipsoid, a polyhedron, or the like. Exemplary irregular shapes may include the shapes of various human organs.

In 604, one of the plurality of data frames may be retrieved. The retrieval of the data frame may be performed by motion identifying unit 306, from the divided data frames as described in 504. The retrieved data frame may indicate the state of the subject during a selected range of time, which may be further processed to represent the motion of the subject in associated with the state of the subject during another selected range of time.

In 606, the motion parameter corresponding to the subject in an arbitrary direction according to the VOI may be determined. In some embodiments, the arbitrary direction may be determined by a user (e.g., an operator) manually. In some embodiments, the arbitrary direction may be determined by an optimization algorithm according to which an updated VOI corresponding to an optimal signal parameter (e.g., the motion parameter or a related parameter) may be determined. The motion parameter corresponding to the subject in an arbitrary direction may be determined by determining a first statistical parameter in a first direction (e.g., the x, y, or z direction) and a second statistical parameter in a second direction (e.g., the x, y, or z direction other than the first direction), and then determining the motion parameter based on the first statistical parameter and the second statistical parameter. As described elsewhere in the disclosure, the VOI may include a plurality of voxels. In some embodiments, the first statistical parameter and/or the second statistical may represent different variances of coincidence distribution of the plurality of voxels about, for example, the reference point as described elsewhere in the disclosure.

In some embodiments, the first statistical parameter, the second statistical parameter, and/or the motion parameter may take form of a second-order moment, a fourth-order moment, or any other order moments. In some embodiments, different kinds of modifications may be applied in the determination of the motion parameters to characterize the motion of the subject. For example, probabilistic distribution of time-of-fly (TOF) may be utilized to optimize the acquired data and/or the direction of motion according to which the motion parameter of the subject is determined. The probability distribution may be estimated based on one or more probability models including a Bernoulli distribution, a Poisson distribution, a uniform distribution, an exponential distribution, a normal distribution, or the like, or a combination thereof. As another example, contribution factors relating to different directions may be taken in account in determining the motion parameter. Details regarding the determination of the motion parameter and exemplary modifications will be described in FIG. 7 and FIG. 8.

In 608, a determination may be made on whether a condition is satisfied. If the condition is satisfied, the process may proceed to 610. If not, the process may go back to 604 to retrieve another data frame, based on which another motion parameter may be determined. In some embodiments, the condition may be whether a predetermined number of motion parameters are determined. In some embodiments, the condition may be whether the motion parameter determined in the last iteration is equal to or substantially equal to one or more parameters determined in one or more previous iterations. As used herein, "substantially equal to" may denote that the difference between two values is below a threshold. The threshold may be a constant value, or may be determined by a proportion of one of the two values.

In 610, motion information of the subject in the arbitrary direction may be determined based on the different pluralities of data frames. The determination of the motion information may be performed by motion identifying unit 306. In some embodiments, the plurality of first statistical parameters and/or the plurality of second statistical parameters may represent different variances of coincidence distribution of the plurality of voxels in the VOI, which reflects a periodical motion of the subject (e.g., the periodic contraction and expansion of the heart) that is determined based on the periodicity of the different pluralities of data frames. The periodicity of the different pluralities of data frames may be analyzed by performing a Fourier transformation on the motion parameters of different pluralities of data frames. Merely by way of example, the periodicity of the cardiac motion may be determined based on the different pluralities of data frames. Furthermore, the cardiac motion information may be determined based on the motion parameters corresponding to different data frames residing in the systolic time interval and diastolic time interval, respectively.

In some embodiments, the motion signal may be further denoised by motion identifying unit 306 based on the periodical motion of the subject. For example, the motion identifying unit 306 may denoise the motion signal by applying a band pass filter. Then, sort the PET dataset may be sorted based on the denoised motion signal by the gating unit 312.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, more than one data frames may be retrieved in 604 based on, for example, the period of the motion, or the data size of each data frame.

Figure 7:
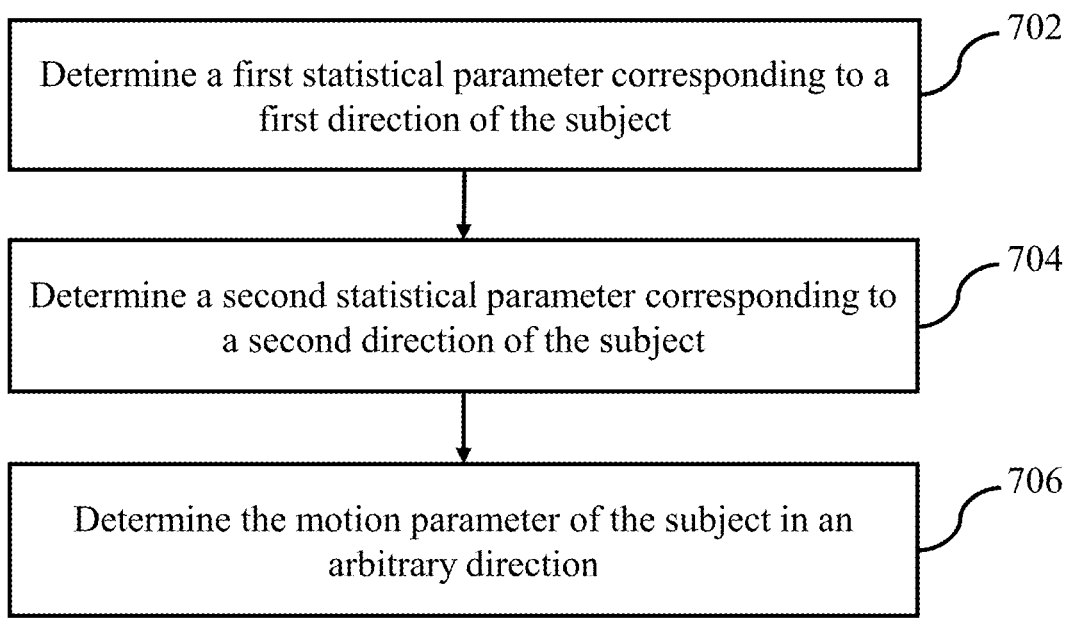
FIG. 7 is a flowchart illustrating an exemplary process of determining the motion parameter according to some embodiments of the present disclosure.

FIG. 7 is a flowchart illustrating an exemplary process of determining the motion parameter according to some embodiments of the present disclosure. In some embodiments, step 606 illustrated in FIG. 6 may be performed based on process 700. In 702, a first statistical parameter may be determined. The first statistical parameter may correspond to the motion of the subject in a first direction. In some embodiments, the first statistical parameter may be determined based on the data frame retrieved as illustrated in steps 603 and 604.

For illustration purpose, the coordinate representation of a coincidence event (represented by LORs) in sinogram coordinate may be depicted in ($\varphi$, s, z, $\theta$, t), corresponding to the list mode data at time t. The specific meaning of the parameters $\varphi$, s, z, $\theta$ may be found in FIG. 9, where $\varphi$ and s represent two sinogram coordinates of the list mode, namely the angle of the projected LOR and the radial distance; $\theta$ represents the angle of the event corresponding to the z direction; and z represents the intersection value of the event and the z axis, which is along the direction of a patient being transported before or during the scanning.

To determine the first statistical parameter, a spatial density value P($\varphi$, s, z, $\theta$, t) representing the list mode data located at the sinogram coordinates ($\varphi$, s, z, $\theta$) at time t may be used. In some embodiments, the spatial density value may be determined by motion identifying unit 306. In some embodiments, the spatial density value P may be determined by counting all events that are detected at time t. As described above, the time t of list mode data may be divided into time frames [i$\Delta$t, (i+1)$\Delta$t], i=0, 1, . . . . In the n-th time frame [n$\Delta$t, (n+1)$\Delta$t], the first statistical parameter may be determined based on the spatial density value P($\varphi$, s, z, $\theta$, t), t$\in$[n$\Delta$t, (n+1)$\Delta$t].

Merely by way of example, the first statistical parameter, representing a variance of coincidence distribution of voxels in the VOI, may take form of a second-order moment as follows:

$$M(S^2(n)) = \int_{\tau=n\Delta T}^{\tau=(n+1)\Delta T} (\int_{VOI} (s-s_c(\varphi))^2 \cdot P(\varphi,s,z,\theta,\tau) d\varphi ds d\theta dz) d\tau, \quad \text{Formula (1)}$$

where $s_c(\varphi)$ represents the radial distance with a projection angle $\varphi$ in the sinogram coordinate, $\tau \in$[n$\Delta$t, (n+1)$\Delta$t] represents the time frame in which the first statistical parameter being determined, and $M(S^2(n))$ denotes the statistical parameter corresponding to the first direction (e.g., radial direction). As used herein, the radial direction may denote a direction that is perpendicular to the direction along the longitudinal axis of the patient (also referred to as "axial direction") along the patient, which may be from the head end of the patient to the tail end of the patient. The VOI may be determined according to step 602 of process 600 illustrated above. For illustration purpose, a VOI in the form of a cylinder may be determined, with the center point of the heart region located in the center of the cylinder. The diameter of the cylinder may be set as 20 cm, and the height of the cylinder may be set as, for example, 20 cm, to enclose the heart region. In some embodiments, in order to determine the mathematical expectation, the VOI may be an integral domain represented in sinogram coordinates.

In 704, a second statistical parameter may be determined. The second statistical parameter may correspond to the motion of the subject in a second direction. In some embodiments, the second statistical parameter may be determined based on the same data frame retrieved for determining the first statistical parameter.

Merely by way of example, the second statistical parameter, representing a variance of coincidence distribution of voxels in the VOI, may take form of a second-order moment as follows:

$$M(Z^2(n)) = \int_{\tau=n\Delta T}^{\tau=(n+1)\Delta T} (\int_{VOI} (z-z_c)^2 \cdot P(\varphi,s,z,\theta,\tau) d\varphi ds d\theta dz) d\tau, \quad \text{Formula (2)}$$

where $z_c$ represents the z coordinate of the reference line in the sinogram coordinate, and $M(Z^2(n))$ denotes the statistical parameter corresponding to the second direction (e.g., axial direction, namely the z direction).

In 706, the motion parameter for the subject in an arbitrary direction may be determined. In some embodiments, the determination of the motion parameter of the subject may be based on the first statistical parameter and/or the second statistical parameter. Merely by way of example, the motion parameter of the subject corresponding to the radial direction, which is represented by E(n), may be determined by:

$$E(n) = \frac{m(S^2(n))}{C(n)}, \quad \text{Formula (3)}$$

where C(n) represents a total count in the VOI, which may in turn be determined by:

$$C(n) = \int_{\tau=n\Delta T}^{\tau=(n+1)\Delta T} (\int_{VOI} P(\varphi,s,z,\theta,\tau) ds d\theta dz) d\tau. \quad \text{Formula (4)}$$

As another example, the motion parameter of the subject corresponding to the axial direction may be determined by:

$$E(n) = \frac{M(Z^2(n))}{C(n)}. \quad \text{Formula (5)}$$

As used herein, formula (3) may correspond to the distribution of the ECT tracer about the central point in image domain corresponding to the radial direction, and formula (5) may correspond to the distribution of the ECT tracer about the central point in image domain corresponding to the axial direction.

Furthermore, in order to determine the motion parameter of the subject in an arbitrary direction, a third statistical parameter may be defined as:

$$M(SZ(n)) = \int_{\tau=n\Delta T}^{\tau=(n+1)\Delta T} (\int_{VOI} (s-s_c(\varphi))(z-z_c) \cdot P(\varphi,s,z,\theta,\tau) d\varphi ds d\theta) d\tau, \quad \text{Formula (6)}$$

where M(SZ(n)) denotes the statistical parameter, corresponding to the co-variance of the first direction and the second direction.

The motion parameter of the subject in an arbitrary direction, which is represented by E(α(n)), may be determined as:

$$E(\alpha(n)) = \frac{M(S^2(n))\sin^2\alpha + M(Z^2(n))\cos^2\alpha + 2M(SZ(n))\sin\alpha\cos\alpha}{C(n)}, \quad \text{Formula (7)}$$

where α denotes the arbitrary angle defined by the deviation from the second direction, namely the z direction herein. E(α(n)) may correspond to the distribution of the ECT tracer within the subject about the central point along the α direction. In some embodiments, the determination of the α direction may be performed by a user (e.g., a doctor) according to, for example, the physiological features of human beings or the specific patient. In some embodiments, the determination of the α direction may be performed by executing a specific program by a processor. The specific program may be designed to determine the optimal direction of the patient such that the motion parameter determined may reflect the motion of the subject with less noise or other disturbances. The specific program may determine the optimal direction from a database storing historical data relating to the patient, or the like.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the second-order moment may be replaced with other forms of statistical parameters. Merely by way of example, the terms $(s-s_c(\varphi))^2$ in formula 1, $(z-z_c)^2$ in formula 2, and $(s-s_c(\varphi))(z-z_c)$ in formula 6 may be replaced by any other even functions, such as, absolute values $|s-s_c(\varphi)|$, $|(z-z_c)|$, and $|(s-s_c(\varphi))(z-z_c)|$, respectively. Other even functions about the reference line/point may also be applicable according to some embodiments of the present disclosure.

Figure 8:
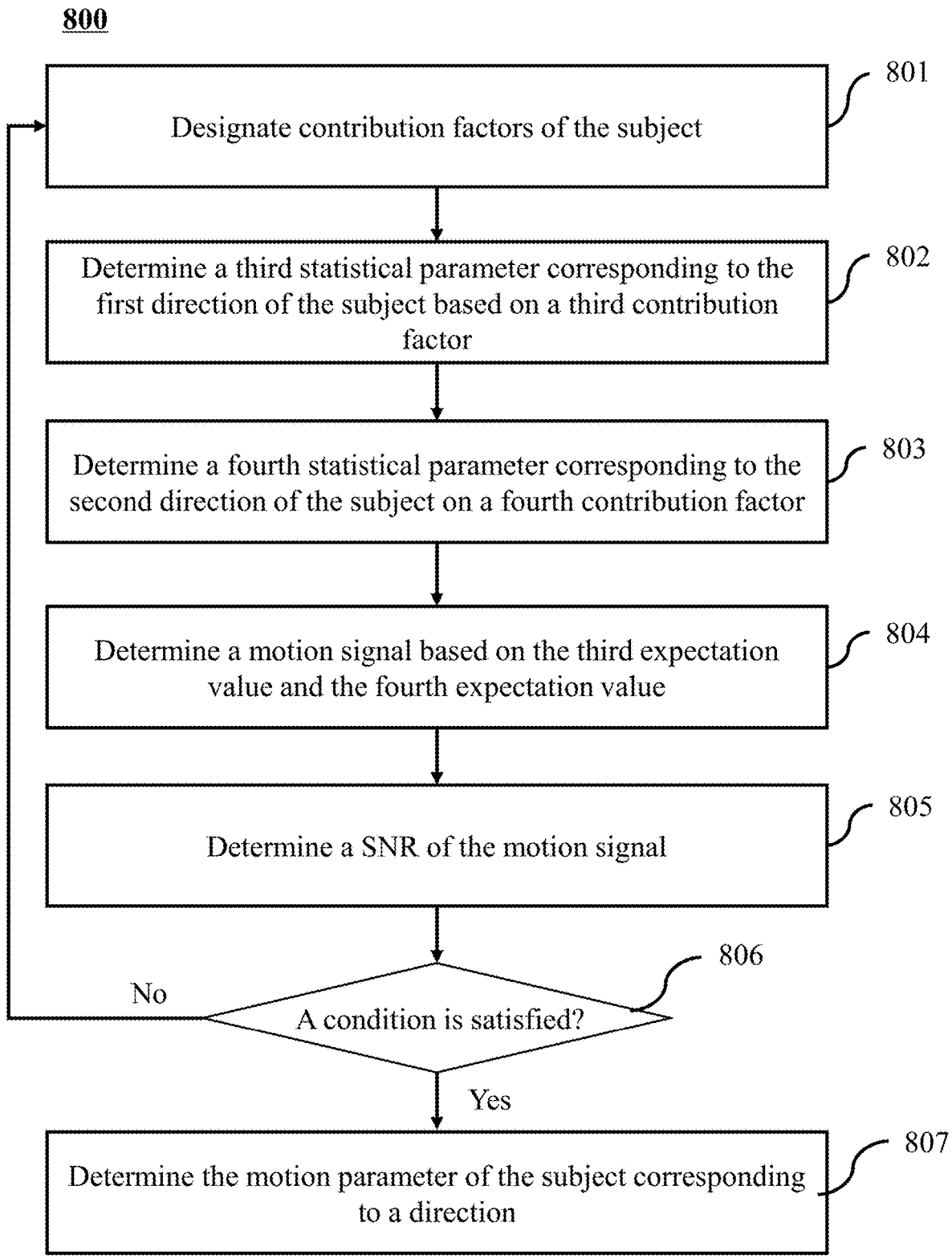
FIG. 8 a flowchart illustrating an exemplary process of determining the motion parameter according to some embodiments of the present disclosure.

FIG. 8 a flowchart illustrating an exemplar process of determining the motion parameter according to some embodiments of the present disclosure. In some embodiments, the step 606 illustrated in FIG. 6 may be performed according to process 800. In 801, contribution factors may be designated. In some embodiments, some of the contribution factors may correspond to the motion of the subject in certain directions. In some embodiments, some of the contribution factors may correspond to the co-variance of different directions. As used herein, the contribution factors may correspond to the determination of the reference line/point (e.g., center point) in a subject, the physiological characteristics of the patient, the determination of a VOI, the signal noise ratio (SNR) in the environment, or the like, or a combination thereof.

In 802, a third statistical parameter based on a third contribution factor may be determined. The third statistical parameter may correspond to the motion of the subject in the first direction. Merely by way of example, the first direction may be designated as the radial direction, and the third statistical parameter, representing a variance of coincidence distribution of voxels in the VOI, may be defined as follows:

$$\hat{M}(S^2(n),V_s) = \int_{\tau=n\Delta T}^{\tau=(n+1)\Delta T} (\int_{VOI} V_s(\varphi,x,z,\theta)(s-s_c(\varphi))^2. \quad \text{Formula (8)}$$

where $\hat{M}(S^2(n), V_s)$ denotes the statistical parameter corresponding to the radial direction, and $V_s(\varphi, s, z, \theta)$ represents the third contribution factor corresponding to the radial direction. In some embodiments, $V_s(\varphi, s, z, \theta) = \beta \sin^2 \alpha$, where α denotes an arbitrary direction as described elsewhere in the disclosure, and β denotes the contribution of the specific point (φ, s, z, θ) in the sinogram coordinate, within the range of [0,1].

In 803, a fourth statistical parameter based on a fourth contribution factor may be determined. The fourth statistical parameter may correspond to the motion of the subject in the second direction. Merely by way of example, the second direction may be designated as the axial direction, and the fourth statistical parameter, representing a variance of coincidence distribution of voxels, may be defined as follows:

$$\hat{M}(Z^2(n),V_z) = \int_{\tau=n\Delta T}^{\tau=(n+1)\Delta T} (\int_{VOI} V_z(\varphi,s,z,\theta)(z-z_c)^2 \cdot P(\varphi,s,z,\theta,\tau) d\varphi ds d\theta dz) d\tau, \quad \text{Formula (9)}$$

where $\hat{M}(Z^2(n), V_z)$ denotes the statistical parameter corresponding to the axial direction, and $V_z(\varphi, s, z, \theta)$ represents the fourth contribution factor corresponding to the axial direction. In some embodiments, $V_z(\varphi, s, z, \theta) = \beta \cos^2 \alpha$.

In 804, a motion signal may be determined based on the third statistical parameter and the fourth statistical parameter. For brevity, the motion signal, which is represented by signal (n, $V_z$, $V_s$, $V_{sz}$), may be defined as:

$$\text{signal}(n, V_Z, V_S, V_{SZ}) = \frac{\hat{M}(S^2(n), V_s) + \hat{M}(Z^2(n), V_Z) + \hat{M}(SZ(n), V_{SZ})}{\hat{C}(n)}, \quad \text{Formula (10)}$$

where $\hat{M}(SZ(n), V_{sz})$ denotes the statistical parameter corresponding to both the radial direction and the axial direction, $V_{sz}$ represents the specific contribution factor corresponding to $\hat{M}(SZ(n), V_{sz})$, and $\hat{C}(n)$ represents the total count in the VOI, with contribution factors taken into account.

In some embodiments, $\hat{M}(SZ(n), V_{sz}), V_{sz}), V_{sz}$, and $\hat{C}(n)$ may be defined as follows:

$$\hat{M}(SZ(n), V_{sz}) = \int_{\tau=n\Delta T}^{\tau=(n+1)\Delta T} (\int_{VOI} V_{sz}(\varphi,s,z,\theta)(s-s_c(\varphi)) (z-z_c) \cdot P(\varphi,s,z,\theta,\tau) d\varphi ds d\theta dz) d\tau, \quad \text{Formula (11)}$$

$$V_{sz}(\varphi,s,z,\theta) = \pm 2(V_z(\varphi,s,z,\theta)V_s(\varphi,s,z,\theta)), \quad \text{Formula (12)}$$

and $$\hat{C}(n) = \int_{\tau=n\Delta T}^{\tau=(n+1)\Delta T} (\int_{VOI} (V_z(\varphi,s,z,\theta) + V_s(\varphi,s,z,\theta)) P(\varphi,s,z,\theta,\tau) ds d\theta dz) d\tau. \quad \text{Formula (13)}$$

In 805, a signal noise ratio (SNR) of the motion signal may be determined. Merely by way of example, a Fourier spectrum analysis may be performed on the signals to determine SNR. As used herein, the SNR may compare the energy level of a target signal within a physiological spectrum, to the energy level of the target signal outside of the physiological spectrum. As used herein, the physiological spectrum may denote the frequency range of a physiological motion, such as cardiac motion, respiratory, or the like, or a combination thereof. See, for example, FIG. 10 for an illustration of the physiological spectrum for a respiratory signal and a cardiac signal. Merely by way of example, the respiration rate of a human being may be 10-20 times per minute, or approximately 0.16-0.30 Hz, and thus a selection of physiological spectrum for a respiratory signal may be chosen between 0 to 0.5 Hz. As another example, the heart rate of a human being may be 50-150 times per minute, or 0.8-2.5 Hz, and thus an exemplary selection of physiological spectrum for a cardiac signal may be chosen between 0.6 to 1.5 Hz. By setting a physiological spectrum for a target signal, the physiological information contained in a target signal may be derived using a spectrum analysis approach. For example, a Fourier analysis may be used to obtain physiological information from the target signal.

The SNR may be determined as follows:

$$SNR(\text{signal}(n, V_Z, V_S, V_{SZ})) = \frac{\int_{f \in \text{signal space}} G_1(FT(\text{signal}(n, V_Z, V_S, V_{SZ}))) df}{\int_{f \notin \text{signal space}} G_2(FT(\text{signal}(n, V_Z, V_S, V_{SZ}))) df} \quad \text{Formula (14)}$$

where FT(signal(t)) is a Fourier transformation of signal(n, $V_z, V_s, V_{sz}$), f∈signal space may indicate that the frequency f falls within the physiological spectrum, and f∉signal space may indicate that the frequency f falls outside of the physiological spectrum. When a cardiac motion needs to be detected, the physiological spectrum for a cardiac signal may be chosen. $G_1$ and $G_2$ may be two functions measuring the energy level of the function g(f), where g(f) may be a function of f, ‖g(f)‖ may be the absolute value of g(f). For example, $G_1$ and $G_2$ may be shown in formula (15) as follows:

$$G_1(g(f)) = G_2(g(f)) = \|g(f)\|^2. \quad \text{Formula (15)}$$

The updated VOI and/or the optimal motion signal may be determined via formula (16) as follows:

$$\text{signal}_c(n) = \underset{V_Z, V_S, V_{SZ}}{\operatorname{argmax}} \ SNR(\text{signal}(n, V_Z, V_S, V_{SZ})). \quad \text{Formula (16)}$$

In some embodiments, discrete values of $V_z, V_s, V_{sz}$ may be utilized by selecting discrete values of α and/or β for solving formula (16). For example, α may be a specific value selected from 0° to 360°, such as, 0°, or 90°, or 180°, or 270°. β may be specific values in the range from 0 to 1, such as 0, or 0.5, or 1. In some embodiments, possible values of α and/or β may be down-sampled such that a preset number of values is processed in determining the updated VOI and/or the optimal motion signal.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the determination of the VOI and/or the direction of motion to determine the motion parameter of the subject may base on the information of time-of-fly (TOF). Specifically, the information of TOF may indicate the volume of the subject in the image reconstruction domain, and the volume of the subject may be further used to optimize the ECT dataset in list mode. Similarly, the optimal direction of motion to determine the motion parameter may also base on the information of TOF. In some embodiments, a probabilistic distribution of time-of-fly (TOF) may be utilized to optimize the VOI and/or the direction of motion according to which the motion parameter of the subject is determined. The probability distribution may be estimated based on one or more probability models including a Bernoulli distribution, a Poisson distribution, a uniform distribution, an exponential distribution, a normal distribution, or the like, or a combination thereof.

Figure 9:
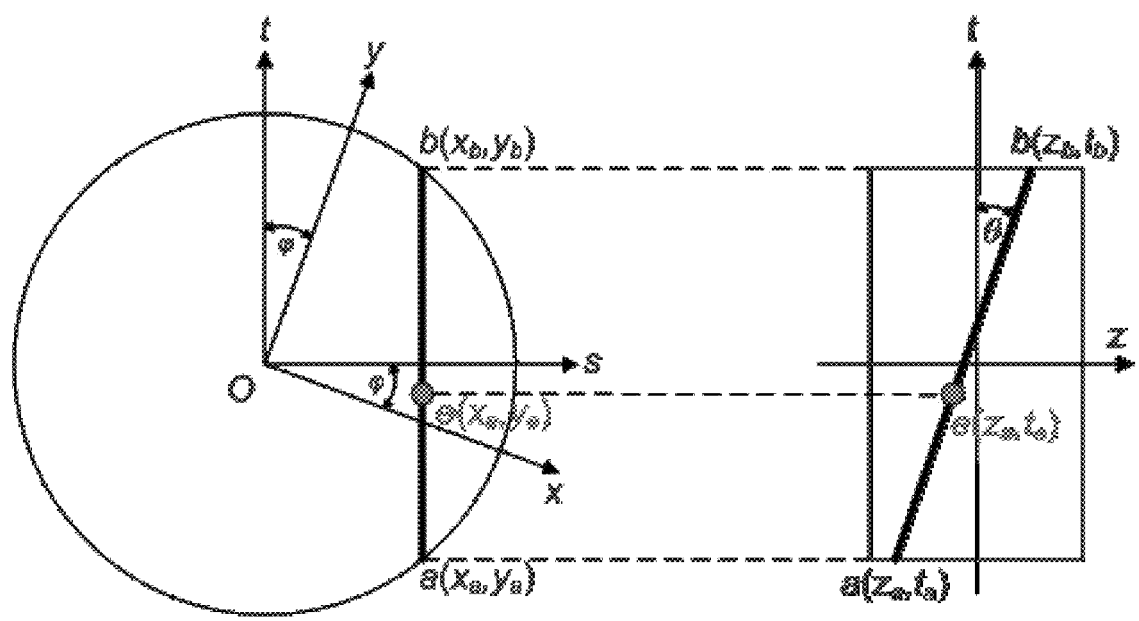
FIG. 9 illustrates a correlation between sinogram coordinates and x-y-z coordinates according to some embodiments of the present disclosure.

FIG. 9 illustrates a correlation between sinogram coordinates and x-y-z coordinates according to some embodiments of the present disclosure. As illustrated in FIG. 9, φ may represent the projection angle, s may represent the projection position, z may represent the axial position, θ may represent the angle of the event corresponding to the z direction; and t may represent the time. The two points $a(x_a, y_a)$ and $b(x_b, y_b)$ may give the two endpoints of the projected line of response, respectively. In FIG. 9, the sinogrm coordinates are illustrated on the left part, and the x-y-z coordinates are illustrated on the right part, where a and b are the indices of the detector pair, e represents an event, $x_e$ represents the x coordinate for the event e, t represents TOF coordinate, and z represents the axial position.

Figure 10:
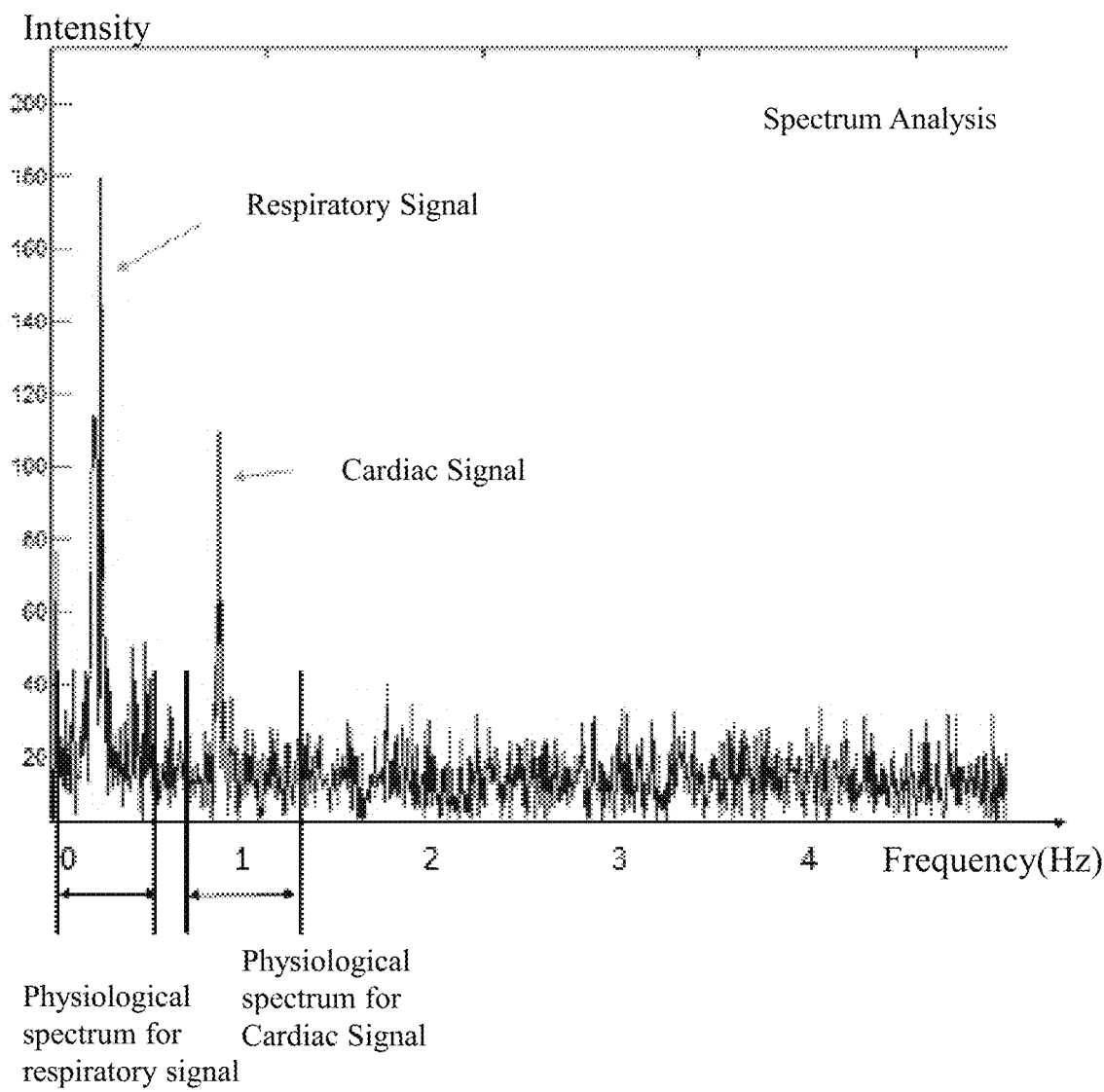
FIG. 10 is an exemplary illustration of the physiological spectrum for a respiratory signal and a cardiac signal according to some embodiments of the present disclosure.

FIG. 10 provides an exemplary illustration of the physiological spectrum for a respiratory signal and a cardiac signal according to some embodiments of the present disclosure. As shown in FIG. 15, the frequency of the respiration rate of a human being may be selected within the physiological spectrum for respiratory signal, e.g., between 0 to 0.5 Hz. The frequency of heart rate of a human being may be selected within the physiological spectrum for cardiac signal, e.g., between 0.6 Hz to 1.5 Hz.

In FIG. 11, (a) illustrates an exemplary signal of the cardiac motion determined according to some embodiments of the present disclosure, and (b) illustrates a signal measured by an external Electrocardiograph (ECG) device. The period of motion illustrated in (a) is about 833 ms, which is approximate to the period of motion illustrated in (b).

Figure 12:
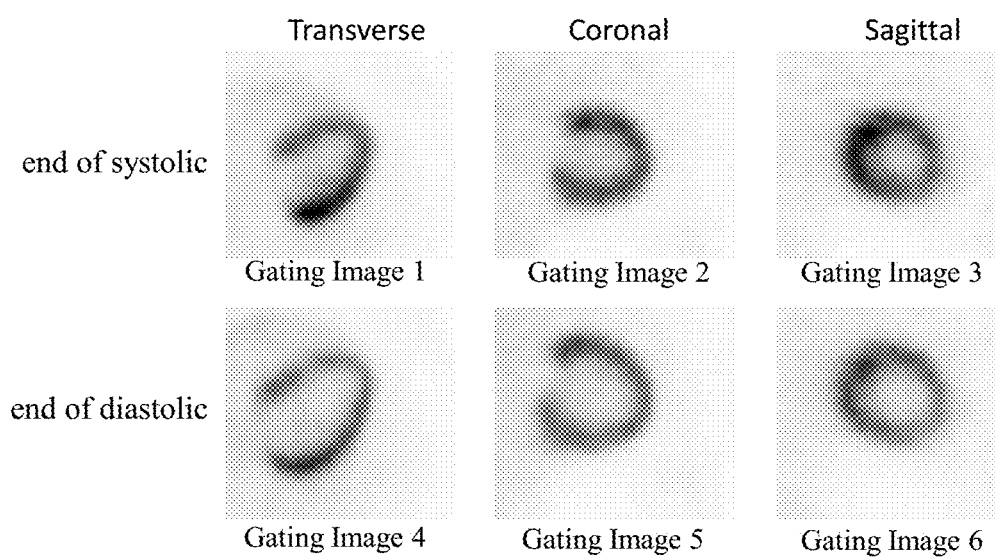
FIG. 12 illustrates exemplary gating images reconstructed based on gated ECT data according to some embodiments of the present disclosure.

FIG. 12 provides exemplary gating images reconstructed based on gated ECT dataset according to some embodiments of the present disclosure. Gating image 1 shows a transverse image of the ventriculus sinister at the end of systole of a human being; gating image 2 shows a coronal image of the ventriculus sinister at the end of systole of the human being; gating image 3 shows a sagittal image of the ventriculus sinister at the end of systole of the human being; gating image 4 shows a transverse image of the ventriculus sinister at the end of diastole of the human being; gating image 5 shows a coronal image of the ventriculus sinister at the end of diastole of the human being; and gating image 6 shows a sagittal image of the ventricles sinister at the end of diastole of the human being.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

We claim:

1. A method implemented on at least one device each of which has at least one processor and storage, the method comprising:
    acquiring an emission computed tomography (ECT) dataset relating to a target organ of a patient;
    determining a motion signal of the target organ that represents a motion of the target organ along a specific direction based on the ECT dataset and a function, the function including a signal noise ratio that relates to the target organ and has a correlation with a direction of the motion of the target organ;

sorting the ECT dataset into a plurality of bins based on the motion signal; and
generating an image of the target organ by reconstructing the plurality of bins,
wherein the determining a motion signal of the target organ comprises:
  determining a reference point of the target organ;
  determining a volume of interest based on the reference point, the volume of interest including a plurality of voxels;
  determining a variance of coincidence distribution of the plurality of voxels about the reference point; and
  determining the motion signal of the target organ based on the variance of coincidence distribution.

2. The method of claim 1, wherein the determining a reference point of the target organ comprises:
  obtaining a CT image including the target organ;
  identifying a first region including the target organ in the CT image; and
  determining the reference point based on a position of the target organ in the first region.

3. The method of claim 1, wherein the determining a reference point is based on a machine learning process.

4. The method of claim 1, wherein the motion signal of the target organ is at least determined by an even function about the reference point.

5. The method of claim 1, wherein the ECT dataset is acquired based on information of time-of-fly.

6. The method of claim 1, wherein the motion signal of the target organ corresponds to a maximum signal noise ratio relating to the target organ.

7. The method of claim 6, wherein the motion signal of the target organ comprises a periodic contraction and expansion motion of the target organ.

8. The method of claim 7, further comprising updating the volume of interest based on the maximum signal noise ratio relating to the target organ.

9. The method of claim 7, further comprising obtaining a denoised motion signal based on the periodic contraction and expansion motion of the target organ by applying a band pass filter, wherein the sorting the ECT dataset is based on the denoised motion signal.

10. The method of claim 1, wherein the determining a variance of coincidence distribution of the plurality of voxels about the reference point comprises:
  determining a second order moment about the reference point.

11. The method of claim 1, wherein the determining a motion signal of the target organ that represents a motion of the target organ along a specific direction based on the ECT dataset and a function comprises:
  designating a candidate direction of the motion of the target organ that corresponds to a maximum signal noise ratio relating to the target organ as the specific direction; and
  determining the motion signal of the target organ based on the specific direction.

12. A system, comprising:
  at least one storage device storing a set of instructions; and
  at least one processor configured to communicate with the at least one storage device, wherein when executing the set of instructions, the at least one processor is directed to cause the system to:
    obtain an emission computed tomography (ECT) dataset relating to a target organ of a patient;
    determine a motion signal of the target organ that represents a motion of the target organ along a specific direction based on the ECT dataset and a function, the function including a signal noise ratio that relates to the target organ and has a correlation with a direction of the motion of the target organ;
    sort the ECT dataset into a plurality of bins based on the motion signal; and
    generate an image of the target organ by reconstructing the plurality of bins,
      wherein to determine the motion signal of the target organ, the at least one processor is further directed to cause the system to:
        determine a reference point of the target organ;
        determine a volume of interest based on the reference point, the volume of interest including a plurality of voxels;
        determine a variance of coincidence distribution of the plurality of voxels about the reference point; and
        determine the motion signal of the target organ based on the variance of coincidence distribution of the plurality of voxels.

13. The system of claim 12, wherein the at least one processor is further directed to cause the system to:
  obtain a CT image including the target organ;
  identify a first region including the target organ in the CT image; and
  determine the reference point based on a position of the target organ in the first region.

14. The system of claim 12, wherein the motion signal of the target organ corresponds to a maximum signal noise ratio relating to the target organ.

15. The system of claim 14, wherein the at least one processor is further directed to cause the system to denoise the motion signal by a band pass filter, wherein the gating unit is configured to sort the PET dataset based on the denoised motion signal.

16. A non-transitory computer readable medium storing instructions, the instructions, when executed by a computing device, causing the computing device to implement a method, comprising:
  acquiring an emission computed tomography (ECT) dataset relating to a target organ of a patient;
  determining a motion signal of the target organ that represents a motion of the target organ along a specific direction based on the ECT dataset and a function, the function including a signal noise ratio that relates to the target organ and has a correlation with a direction of the motion of the target organ;
  sorting the ECT dataset into a plurality of bins based on the motion signal; and
  generating an image of the target organ by reconstructing the plurality of bins,
  wherein the determining a motion signal of the target organ comprises:
    determining a reference point of the target organ;
    determining a volume of interest based on the reference point, the volume of interest including a plurality of voxels;
    determining a variance of coincidence distribution of the plurality of voxels about the reference point; and
    determining the motion signal of the target organ based on the variance of coincidence distribution of the plurality of voxels.

* * * * *